United States Patent
Gaudio et al.

(10) Patent No.: US 11,471,459 B2
(45) Date of Patent: Oct. 18, 2022

(54) COMPOUNDS WITH ENHANCED ANTI-TUMOR EFFECTS

(71) Applicant: FONDAZIONE PER L'ISTITUTO ONCOLOGICO DI RICERCA (IOR), Bellinzona (CH)

(72) Inventors: Eugenio Gaudio, Bellinzona (CH); Francesco Bertoni, Bellinzona (CH); Natalina Pazzi, Tortona (IT); Matilde Guala, Valmacca (IT)

(73) Assignee: FONDAZIONE PER L'ISTITUTO ONCOLOGICO DI RICERCA (IOR), Bellinzona (CH)

( * ) Notice: Subject to any disclaimer, the term of this patent is extended or adjusted under 35 U.S.C. 154(b) by 135 days.

(21) Appl. No.: 16/981,826

(22) PCT Filed: Mar. 26, 2018

(86) PCT No.: PCT/EP2018/057678
§ 371 (c)(1),
(2) Date: Sep. 17, 2020

(87) PCT Pub. No.: WO2019/185117
PCT Pub. Date: Oct. 3, 2019

(65) Prior Publication Data
US 2021/0113565 A1    Apr. 22, 2021

(51) Int. Cl.
| C07D 487/04 | (2006.01) |
| A61K 45/06 | (2006.01) |
| A61P 35/02 | (2006.01) |
| A61K 31/519 | (2006.01) |

(52) U.S. Cl.
CPC ............ *A61K 31/519* (2013.01); *A61K 45/06* (2013.01); *A61P 35/02* (2018.01); *C07D 487/04* (2013.01)

(58) Field of Classification Search
CPC ..... C07D 487/04; A61P 35/02; A61K 31/519; A61K 45/06
See application file for complete search history.

(56) References Cited

FOREIGN PATENT DOCUMENTS

| EP | 2842945 A1 | 3/2015 |
| WO | 2008023161 A1 | 2/2008 |
| WO | 2017041536 A1 | 3/2017 |
| WO | WO 2017/041536 | * 3/2017 | ........... C07D 471/04 |

OTHER PUBLICATIONS

Stanovnik, et al.: "Heteroacyl Azides as Acylating Agents for Aromatic or Heteroaromatic Amines", J. Heterocyclic Chem., vol. 17, 1980, pp. 733-736.
International Search Report issued in corresponding PCT Application No. PCT/EP2018/057678 dated Jun. 20, 2018.
Sehn, L.H., et al. (2015) Diffuse large B-cell lymphoma: optimizing outcome in the context of clinical and biologic heterogeneity. Blood, 125, 22-32.
Siegel, R.L., et al. (2016) Cancer statistics, 2016. CA Cancer J Clin, 66, 7-30.
Stewart, B., et al. (eds.) (2014) World Cancer Report 2014 IARC Nonserial Publication, pp. 1-632 (uploaded in three sections).
Swerdlow, S.H., et al. (2016) The 2016 revision of the World Health Organization classification of lymphoid neoplasms Blood, 127, 2375-2390.
Testoni, M., et al.(2015) Genetic lesions in diffuse large B-cell lymphomas. Ann Oncol, 26, 1069-1080.

* cited by examiner

*Primary Examiner* — Erich A Leeser
(74) *Attorney, Agent, or Firm* — Carter, DeLuca & Farrell LLP

(57) ABSTRACT

The compounds of formula (I)

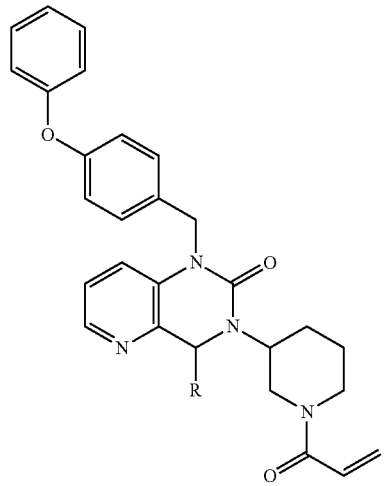

where the group —R may represent =O or —H, are new anti-proliferative agents with remarkable anti-tumour effects in-vivo, showing in particular a wide spectrum of activities in respect of lymphomas of different origin.

14 Claims, 6 Drawing Sheets

COMPOUNDS WITH ENHANCED ANTI-TUMOR EFFECTS

BACKGROUND

Despite progress in pharmaceutical and medical research, tumors still represent a great challenge for life quality and life expectation. Among them, lymphomas, including chronic lymphocytic leukemia, are a group of tumors originating from lymphoid cells (Swerdlow, et al 2016) and are among the most common cancers, accounting for approximately 5% of all new cases in adults and up to 25% in children and adolescents (Siegel, et al 2016, Stewart and Wild 2014). Lymphomas comprise over 60 different entities or provisional entities that are distinguished based on a combination of histological, immunophenotypic, genetic and clinical features (Swerdlow, et al 2016). The most common lymphoma subtype is the diffuse large B-cell lymphoma (DLBCL), accounting for 30%-40% of all lymphomas (Sehn and Gascoyne 2015), and that includes at least two main subtypes, the germinal center B-cell (GCB) type and the activated B-cell like (ABC) type (Sehn and Gascoyne 2015, Swerdlow, et al 2016, Testoni, et al 2015). Most DLBCL patients are cured with regimens such as R-CHOP (rituximab, cyclophosphamide, doxorubicin, vincristine, and prednisone), but 30-40% of them present with a refractory disease or experience a relapse indicating the need of further therapeutics. Ibrutinib (Imbruvica) is a small molecule drug with structure:

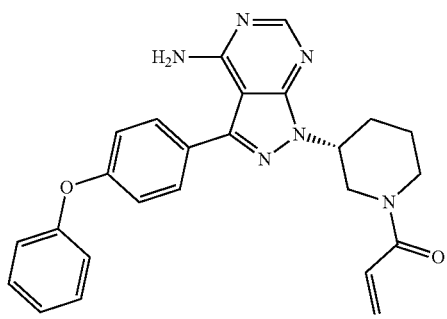 [SMILES: C=CC(=O)N1CCC[C@@H](n2nc(-c3ccc(Oc4ccccc4)cc3)c3c(N)ncnc32)C1]

that binds permanently to a protein, Bruton's tyrosine kinase (BTK), that is important in B cells; the drug is used to treat B cell cancers.

At present, the search for antitumor agents is still ongoing in the effort to widen the spectrum of available products, reduce the unwanted side effects, provide for alternatives in case if drug resistance, identify antitumor agents with sufficiently broad spectrum of activity and/or preferential activity on specific forms of tumors. In particular, liquid tumors like lymphomas and leukemias remain an important area of research, due to the relatively low number of effective products approved in therapy.

SUMMARY

The present Applicant has synthetized new compounds having the following structure (I)

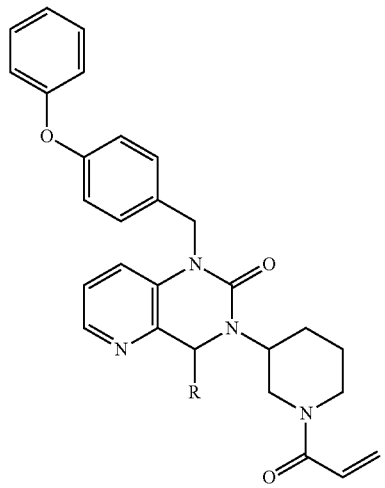

where the group —R may represent =O or —H. Biological testing showed, for the present compounds, an unexpected, potent anti-proliferative activity, with remarkable anti-tumour effects in-vivo; in particular, a wide spectrum of activity on lymphomas and leukaemias of various origin/symptomatology, such as: B-cell lymphomas, Hodgkin lymphoma, T-cells lymphomas, chronic lymphocytic leukaemia, T-cell leukaemias, etc. The present inventions concerns the compounds of formula (I) per se, as well as their use in therapy, in treating tumours, in particular leukemias and lymphomas; the invention also includes a process of production of the instant compounds, as well as pharmaceutical compositions containing them.

DETAILED DESCRIPTION

Figure 1:
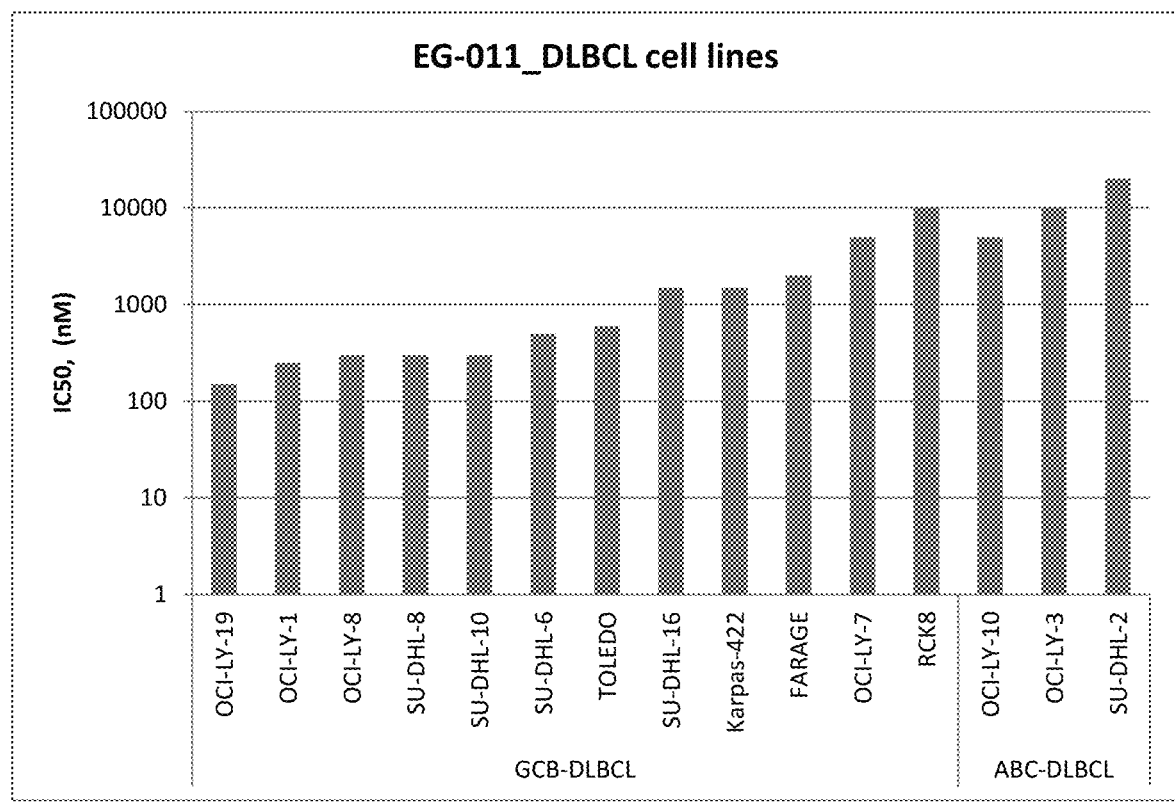
FIG. 1. Distribution of IC50 values for EG-011 in 15 DLBCL cell lines. Cell lines were treated for 72 h. X-axis, ABC, activated B cell-like DLBCL; GCB, germinal center B cell DLBCL. Y-axis, IC50 values in nM.

Main object of the present invention are the compounds of formula (I) as such

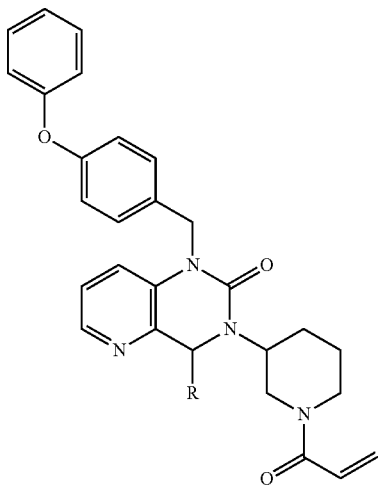

(I)

where the group —R may represent =O or —H.

The compound wherein —R is =O has chemical name: 1-[(4-phenoxyphenyl)methyl]-3-(1-prop-2-enoyl-3-piperidyl)pyrido[3,2-d]pyrimidine-2,4-dione (also briefly identified herein as "EG-011") The compound wherein —R is —H has chemical name: 1-[(4-phenoxyphenyl)methyl]-3-(1-prop-2-enoyl-3-piperidyl)pyrido[3,2-d]pyrimidine-2-one.

In the present invention, the compounds of formula (I) are used as such, or as pharmaceutically acceptable salt thereof. As used herein, the term "pharmaceutically acceptable" means that which is useful in preparing a pharmaceutical composition that is generally safe, non-toxic and neither biologically nor otherwise undesirable and includes that which is acceptable for veterinary use as well as human pharmaceutical use. Pharmaceutically acceptable salts of the compounds of formula (I) are typically, though not limitedly, those resulting from the protonation of one or more of its nitrogen atoms (I); in such salts, the compounds of formula (I) will normally be in cationic form, coupled to a suitable counter anion; non-limiting examples of counter anions are chloride, bromide, sulphate, sulfonate, aminosulfonate, phosphate, phosphonate, formate, carbonate, acetate, propionate, butyrate, fumarate, maleate, mesylate, citrate, oxalate, pivalate, etc. The compounds of formula (I) can also be used in a prodrug form, for example as a pharmaceutically acceptable ester which, after administration, can hydrolize and thus release the compound of formula (I) as such. All such forms are meant to be included for use in the present invention, As used herein, the terms "tumour" or "anti-tumour" or "use as anti-tumour agent" or "tumour diseases", refer to any diseases characterized by the formation and proliferation of tumour cells; the above terms include carcinomas, lymphomas, leukemias, sarcomas, myelomas, and the corresponding mixed-type forms; the above terms are inclusive of solid and liquid tumors. Preferred liquid tumors are leukemias and lymphomas. Among the leukemias, particular interest is attached to chronic lymphocytic leukaemia, T cell leukaemia, e.g. acute T cell leukaemia. Among the lymphomas, particular interest is attached to B cell lymphomas, e.g. diffuse large B cell lymphomas (such as activated B cell-like diffuse large B cell lymphoma, or germinal center B cell diffuse large B cell lymphoma), mantle cell lymphoma, Hodgkin lymphoma, non-Hodgkin lymphoma, T cell lymphomas, e.g. cutaneous T-cell lymphoma, peripheral T cell lymphoma, anaplastic large T cell lymphoma, etc.

The treatment or prevention tumour diseases by means of one or more compounds of formula (I) represents a further object of the present invention. Accordingly, in one embodiment, the invention concerns the above described compounds of formula (I) or pharmaceutically acceptable salt thereof for use as anti-tumour agent, i.e. for the treatment or prevention of tumour diseases; in another embodiment, the invention concerns the use of the compound of formula (I) or pharmaceutically acceptable salt thereof for manufacturing a medicament for the treatment or prevention of tumour diseases. The invention extends to the compounds of formula (I) or pharmaceutically acceptable salt thereof for use in medicine.

As used herein, "treatment" or "treating" means the administration of the instant compound to a subject (human or animal) who has already shown one or more symptoms of said tumour; The term "treatment," further refers to the medical management of a patient with the intent to cure, ameliorate, stabilize, or prevent the relevant disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder.

As used herein, "prevention" or "preventing" means the administration of the instant compounds to a subject who shows unclear symptoms or no symptoms of said tumour diseases, but who is at risk of developing them, for example by being in contact with tumorigenic substances in the environment, being genetically predisposed to develop tumour diseases, etc.; a preventative treatment is generally directed to minimizing or partially or completely inhibiting the development of the associated tumor disease.

The compounds of formula (I) or pharmaceutically acceptable salt thereof can be administered in a variety of dosages and regimens in function of the type/severity of the tumour disease, the conditions/age of the patient, and the chosen administration route. As non-limitative indication, dosages may vary between 10 and 500 mg/Kg, preferably between 100 and 300 mg/Kg, of the compound of formula (I) expressed as free base; regimens may involve administration of the above dosages for one or more days a week, e.g. 2, 3, 4, 5, 6 or 7 days a week, for one, two, three or more weeks as needed. Conveniently, the compounds of formula (I) or pharmaceutically acceptable salt thereof will be supplied to patients as one or more dosage units, each containing the aforementioned dosage amounts.

The compounds of formula (I) or pharmaceutically acceptable salt thereof may be administered via any possible administration route, e.g. oral, peroral, buccal, sublingual, inhalatory, intramuscular, intravenous, topical, percutaneous, transcutaneous, rectal, etc., as dictated by convenience and/or medical reasons. Depending on the chosen administration route, the compound of formula (I) or pharmaceutically acceptable salt thereof will be formulated in a correspondingly suitable administration form. Non-limitative mention can be made herein to tablet, pill, capsule, microcapsule, granule, microgranule, pellet, micropellet, powder, lyophilized powder, solution, suspension or emulsion, film, gel, cream, percutaneous or transdermal delivery system, e.g. patch, plaster, etc. Wherever possible the administration form will be supplied to patients as one or more dosage units as defined above.

Further object of the invention is a pharmaceutical composition comprising the above described compounds of formula (I) or pharmaceutically acceptable salt thereof. In such compositions, the compounds of formula (I) or pharmaceutically acceptable salt thereof will be in presence of one or more pharmaceutical excipients.

The choice of the excipients will depend by enlarge from the chosen administration form. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a gliding such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. The compounds can be administered as a component of an elixir, suspension, syrup, wafer, orally disintegrating film, orally disintegrating tablet, chewing gum. A syrup may contain, in addition to the active compounds, sucrose as a sweetening agent and certain preservatives, dyes and colorings and flavors. Solutions or suspensions used for injection can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride, mannitol and dextrose. An injectable preparation, can be enclosed in ampoules, disposable syringes or multiple dose vials made of glass or plastic.

A further object of the invention is a process of preparing the aforementioned pharmaceutical compositions, comprising formulating (e.g. admixing or contacting) the compounds of formula (I) or pharmaceutically acceptable salt thereof with one or more pharmaceutical excipients.

For use in therapy, the compounds of formula (I) or pharmaceutically acceptable salt thereof may be administered alone or (alternatively) with further active agents, in particular further anti-tumour agents. In the latter case, the relevant combination treatment may be performed by administering dosage forms in which both active agents are co-formulated together or (alternatively) by administering, within suitable time windows, separate dosage forms containing one or the other active agent.

Examples of further anti-tumour agents suitable for said combination treatment are: Methotrexate, Paclitaxel, Brentuximab, Adriamycin, Afatinib, Imiquimod, Alectinib, Alemtuzumab, Pemetrexed, Melphalan, Brigatinib, Chlorambucil, Aminolevulinic Acid, Pamidronate, Ofatumumab, Atezolizumab, Avastin, Avelumab, Azacitidine, Avelumab, Carmustine, Belinostat, Inotuzumab Ozogamicin, Bevacizumab, Bexarotene, Bicalutamide, Bleomycin, Blinatumomab, Bortezomib, Bosutinib, Brentuximab, Brigatinib, Cabazitaxel, Acalabrutinib, Alemtuzumab, Irinotecan, Capecitabine, Fluorouracil, Carboplatin, Carfilzomib, Ceritinib, Daunorubicin, Cetuximab, Chlorambucil, Cisplatin, Cladribine, Cyclophosphamide, Clofarabine, Clofarabine, Cobimetinib, Cometriq, Copanlisib, Dactinomycin, Cobimetinib, Crizotinib, Cyclophosphamide, Ifosfamide, Ramucirumab, Cytarabine, Cytarabine, Dabrafenib, Dacarbazine, Dacogen, Dactinomycin, Daratumumab, Daratumumab, Dasatinib, Daunorubicin, Decitabine, Defibrotide, Degarelix, Denosumab, Dexamethasone, Dexrazoxane, Dinutuximab, Docetaxel, Doxorubicin, Dacarbazine, Fluorouracil, Epirubicin Hydrochloride, Elotuzumab, Oxaliplatin, Elotuzumab, Enasidenib, Enzalutamide, Epirubicin, Cetuximab, Eribulin, Erivedge, Erlotinib, Amifostine, Etoposide, Doxorubicin, Raloxifene, Exemestane, Toremifene, Panobinostat, Fulvestrant, Fludarabine, Fluorouracil, Flutamide, Obinutuzumab, Gefitinib, Gemcitabine, Eribulin, Trastuzumab, Topotecan, Palbociclib, Ibritumomab, Ibrutinib, Ponatinib, Idarubicin, Idelalisib, Enasidenib, Ifosfamide, Imatinib, Durvalumab, Imiquimod, Inotuzumab Ozogamicin, Ipilimumab, Gefitinib, Irinotecan, Romidepsin, Ixabepilone, Ixazomib, Ixabepilone, Ruxolitinib, Cabazitaxel, Pembrolizumab, Ribociclib, Tisagenlecleucel, Carfilzomib, Lapatinib, Olaratumab, Lenalidomide, Lenvatinib, Letrozole, Leucovorin, Leuprolide, Lomustine, Olaparib, Vincristine, Procarbazine, Mechlorethamine, Trametinib, Mercaptopurine, Mesna, Temozolomide, Methotrexate, Methylnaltrexone, Midostaurin, Mitomycin C, Mitoxantrone, Vinorelbine, Necitumumab, Nelarabine, Neratinib, Sorafenib, Nilutamide, Nilotinib, Ixazomib, Niraparib, Nivolumab, Tamoxifen, Obinutuzumab, Ofatumumab, Olaparib, Olaratumab, Omacetaxine, Nivolumab, Osimertinib, Oxaliplatin, Paclitaxel, Palbociclib, Palifermin, Panitumumab, Panobinostat, Carboplatin, Pembrolizumab, Pertuzumab, Ponatinib, Necitumumab, Pralatrexate, Procarbazine, Denosumab, Ramucirumab, Rasburicase, Regorafenib, Methylnaltrexone, Lenalidomide, Ribociclib, Rituximab, Romidepsin, Rucaparib, Siltuximab, Sonidegib, Sorafenib, Dasatinib, Regorafenib, Sunitinib, Siltuximab, Omacetaxine, Thioguanine, Dabrafenib, Osimertinib, Erlotinib, Targretin, Nilotinib, Taxol, Taxotere, Atezolizumab, Temozolomide, Temozolomide, Thiotepa, Topotecan, Toremifene, Trabectedin, Trametinib, Bendamustine, Lapatinib Ditosylate, Dinutuximab, Valrubicin, Vandetanib, Panitumumab, Vinblastine, Bortezomib, Vemurafenib, Abemaciclib, Vinorelbine, Vismodegib, Vorinostat, Pazopanib, Crizotinib, Ipilimumab, Trabectedin, Ibritumomab, Goserelin, Zoledronic Acid, Ceritinib, pharmaceutically acceptable salts, esters or derivatives thereof.

A further object of the present invention is a process for the preparation of the compound of formula (I) or pharmaceutically acceptable salt thereof, where said compound is obtained from one or more suitable precursors. Typical precursors are those represented as formulas (1) to (7) in the Scheme 1 here below, with reference to the compound where —R is =O.

Scheme 1

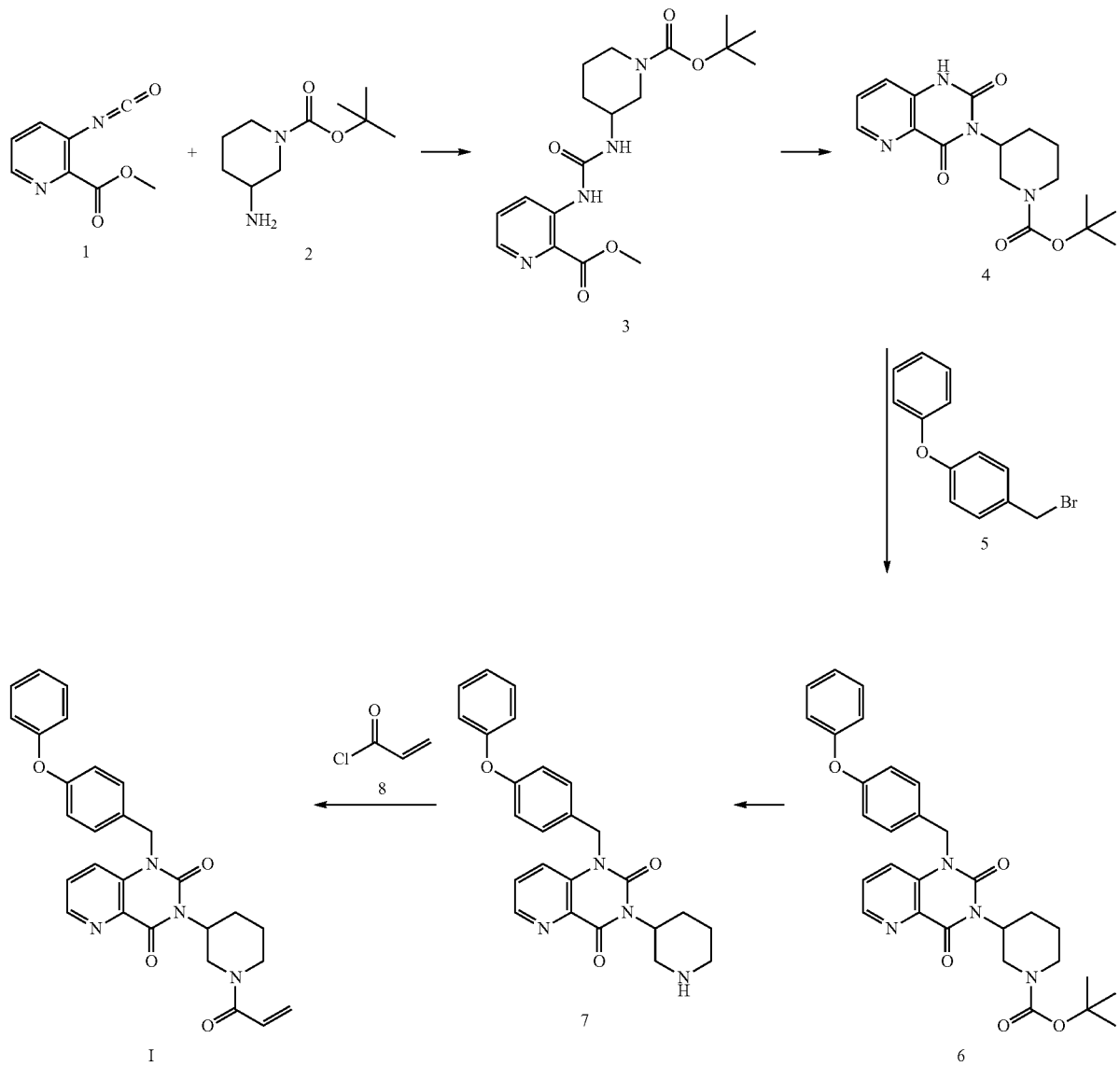

Processes which can be used and are described and reported in detail in the following examplifications; yet they should not be viewed as limiting the scope of the synthetic methods available for the preparation of the compound of the invention. Where the preparation of starting materials is not described, these are commercially available, known in the literature, or readily obtainable by those skilled in the art using standard procedures. Any of the compounds and intermediates showed herein which are racemic, may also exist and be used as enantiomers.

An intermediate of formula (3), may be prepared according to Scheme 1 reported above by reaction of 3-isocyanatepyridine-2-carboxylate 1 with tert-butyl 3-aminopiperidine-1-carboxylate 2. Typical reaction conditions comprise reacting 3-isocyanatepyridine-2-carboxylate 1 with tert-butyl 3-aminopiperidine-1-carboxylate 2 in a suitable polar aprotic solvent, such as DC M, at an appropriate temperature such as, for example, at room temperature.

An intermediate compound of formula (4), may be prepared according to Scheme 1 reported above by reaction of methyl 3-[(1-tert-butoxycarbonyl-3-piperidyl)carbamoylamino]pyridine-2-carboxylate 3 with sodium ethoxide. Typical reaction conditions comprise reacting methyl 3-[(1-tert-butoxycarbonyl-3-piperidyl)carbamoylamino]pyridine-2-carboxylate 3 with a 20% solution of sodium ethoxide in EtOH, in a suitable alcohol, such as MeOH or EtOH, at an appropriate temperature such as, for example, ranging from 65 to 80° C.

An intermediate of formula (6), may be prepared according to Scheme 1 reported above by alkylation of tert-butyl 3-(2,4-dioxo-1H-pyrido[3,2-d]pyrimidin-3-yl)piperidine-1-carboxylate 4 with 1-(bromomethyl)-4-phenoxy-benzene 5. Typical reaction conditions comprise reacting tert-butyl 3-(2,4-dioxo-1H-pyrido[3,2-d]pyrimidin-3-yl)piperidine-1-carboxylate 4 with 1-(bromomethyl)-4-phenoxy-benzene 5, in the presence of an appropriate base, such as, for example, $K_2CO_3$, in a suitable polar aprotic solvent, such as DMF, at an appropriate temperature such as, for example, at room temperature.

An intermediate of formula (7) may be prepared according to Scheme 1 reported above by deprotection of tert-butyl 3-[2,4-dioxo-1-[(4-phenoxyphenyl)methyl]pyrido[3,2-d]pyrimidin-3-yl]piperidine-1-carboxylate 5 in an acidic medium. Typical reaction conditions comprise reacting tert-butyl 3-[2,4-dioxo-1-[(4-phenoxyphenyl)methyl]pyrido[3,2-d]pyrimidin-3-yl]piperidine-1-carboxylate 6 with an acid, such as, for example, 4M HCl in dioxane, in a suitable polar aprotic solvent, such as DCM, at an appropriate temperature such as, for example, ranging form 0° to r.t. [see, for a general reference, T. W. Green; Protective Groups in Organic Synthesis (Wiley, N.Y. 1981)].

The compound of formula (I) in which —R is =O may be prepared according to Scheme 1 reported above by acylation of 1-[(4-phenoxyphenyl)methyl]-3-(3-piperidyl)pyrido[3,2-d]pyrimidine-2,4-dione 7 with acryloyl chloride 8. Typical reaction conditions comprise reacting 1-[(4-phenoxyphenyl)methyl]-3-(3-piperidyl)pyrido[3,2-d]pyrimidine-2,4-dione 7 with acryloyl chloride 8, in the presence of an appropriate base, such as, for example, TEA, in a suitable polar aprotic solvent, such as DCM, at an appropriate temperature such as, for example, at room temperature. For synthesis of the compound of formula (I) in which —R is —H, reference can be made to the above scheme 1 reactions, suitably modified in that the corresponding precursors, intermediates and final product bear the same modification of —R.

The invention is described next with reference to the following non-limiting examples.

EXPERIMENTALS

Example 1: Synthesis and Chemical Characterization of Compound (I) EG-011

Chemical names of compounds are generated with BIOVIA Draw 2017 R2 tool. The solution of common inorganic salts used in workups are aqueous solutions.
Abbreviations:

| | |
|---|---|
| DCM | Dichloromethane |
| DMF | N,N-Dimethylformamide |
| EtOAc | Ethylacetate |
| MeOH | Methanol |
| TEA | Triethylamine |
| TFA | Trifluoroacetic acid |
| h | hour |
| eq | equivalents |
| min | minutes |
| r.t. | room temperature |
| Rt | retention time |
| sat. | saturated |

NMR Characterization:

Proton Magnetic Resonance ($^1$H NMR) spectra were collected using deuterated solvents (DMSO-$d_6$) to 25° C. on Bruker Avance 300 MHz. Chemical shifts are expressed in parts per million (ppm) and measured using the residual solvent signals as the reference. Multiplicity is indicated as follows: (s) singlet, (d) doublet, (dd) double doublet, (t) triplet, (q) quartet, (m) multiplet, (br s) broad signal.

LC/UV/MS Analytical Method:

The MS/ESI$^+$ [MH]$^+$ values reported in the text below may be obtained by Mass Spectrometer ZQ or equivalent:

MS instrument: Waters ZQ (or equivalent)

Polarity: ES+

Capillary (kV): 3.50

Cone (V): 20.00

Extractor (V): 2.00

RF Lens (V): 0.2

Source Temperature (° C.): 130

Desolvation Temperature (° C.): 350

Desolvation Gas Flow (L/hr): 600

Mass range (Da): 50 to 900

Scan time (sec): 0.6

Inter-Scan delay (sec): 0.2

LC instrument: Waters Alliance e2695

Instrument: HPLC Waters with Photodiode Detector 2998, Column Oven and Mass Spectrometer ZQ or equivalent Column: Phenomenex Gemini-NX C18, 150×2.0, 3 μm or equivalent Column Temperature (° C.): 25

Wavelength (nm): 215

Flow (mL/min): 0.2

Injection volume (μL): 5

Mobile phase solvent A: ($H_2O$+0.1% Formic acid); mobile phase solvent B (Acetonitrile+0.1% Formic acid.

Gradient:

| T (min) | % A | % B |
|---|---|---|
| 0 | 80 | 20 |
| 15 | 30 | 70 |
| 35 | 30 | 70 |

Flash chromatography purifications were performed using a Biotage Isolera autopurification system, and carried out over pre-packed Biotage SNAP KP-Sil cartridges, Biotage SNAP Ultra or Biotage SNAP KP-NH cartridges.

Brine refers to a saturated aqueous solution of NaCl.

The compound of structure (I) could be prepared following the synthetic route depicted in Scheme 2:

Scheme 2

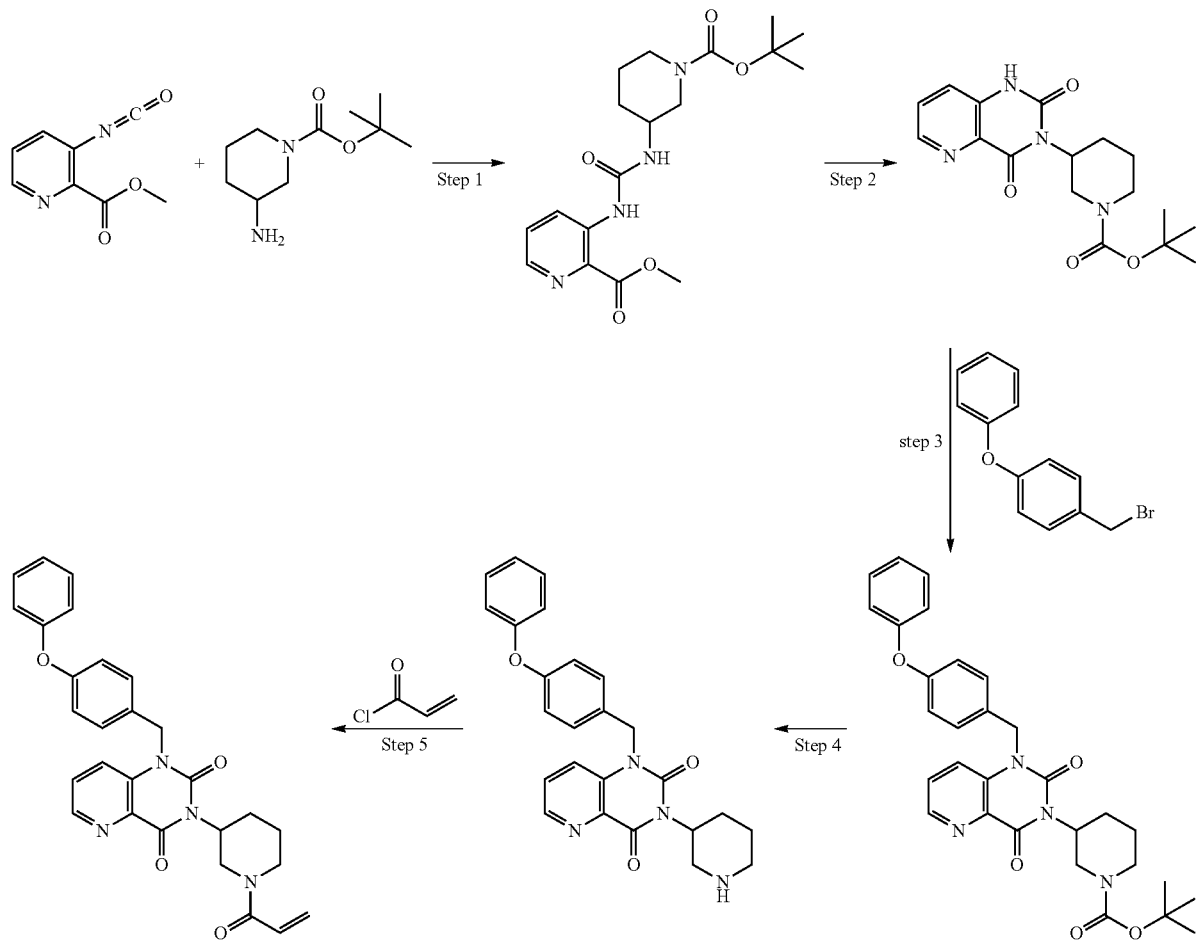

Step 1: synthesis of methyl 3-[(1-tert-butoxycarbonyl-3-piperidyl)carbamoylamino]pyridine-2-carboxylate

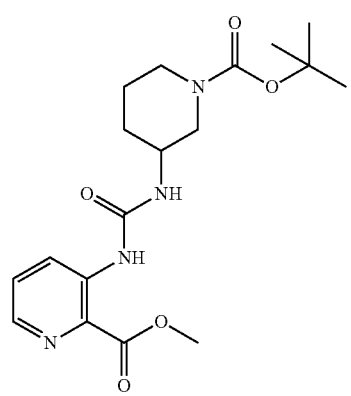 [SMILES: COC(=O)c1ncccc1NC(=O)NC1CCCN(C(=O)OC(C)(C)C)C1]

To a solution of 3-isocyanatepyridine-2-carboxylate (prepared as described in *Synthetic Communications*, 2003, 33(24), 4259-4268; 1.20 g, 6.736 mmol) in dry dichloromethane (8 mL), a solution of racemic tert-butyl 3-aminopiperidine-1-carboxylate (1.349 g, 6.736 mmol) in DCM (4 mL) was added drop-wise and the resulting mixture was stirred at room temperature overnight. After evaporation of the solvent at reduced pressure, the residue was purified by flash chromatography on Biotage KP-Sil SNAP cartridge (DCM:EtOAc=80:20 to 100% EtOAc). A further purification by flash chromatography on Bitotage NH SNAP cartridge (hexane:EtOAc=80:20 to 40:60) was required to afford title compound (1.4 g). MS/ESI$^+$379.1 [MH]$^+$, Rt=13.6 min Step 2: Synthesis of tert-butyl 3-(2,4-dioxo-1H-pyrido[3,2-d]pyrimidin-3-yl)piperidine-1-carboxylate To a solution of methyl 3-[(1-tert-butoxycarbonyl-3-piperidyl)carbamoylamino]pyridine-2-carboxylate (1.3 g) in MeOH (15 mL), 20% sodium ethoxide solution in EtOH (1.48 mL, 3.8 mmol) was added and the resulting mixture was heated to reflux for 8 h, then stirred at room temperature overnight. The mixture was evaporated to dryness together with a smaller batch (obtained by reacting 0.100 g of methyl 3-[(1-tert-butoxycarbonyl-3-piperidyl)carbamoylamino] pyridine-2-carboxylate under the same conditions) and the residue was dissolved in water and acidified with acetic acid (pH≈4-5). The precipitate was collected by filtration and washed several times with plenty of water. The solid was dried under vacuum at 50° C. affording title compound as a beige solid (1.1 g, 3.175 mmol, 47% yield over 2 steps). MS/ESI$^+$347.0 [MH]+, Rt=11.8 min Step 3: synthesis of tert-butyl 3-[2,4-dioxo-1-[(4-phenoxyphenyl)methyl]pyrido[3,2-d]pyrimidin-3-yl]piperidine-1-carboxylate

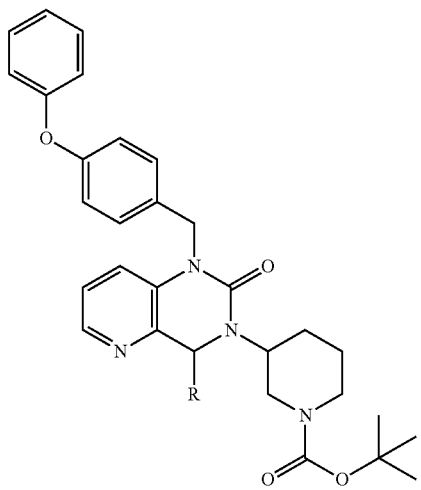

To a suspension of tert-butyl 3-(2,4-dioxo-1H-pyrido[3,2-d]pyrimidin-3-yl)piperidine-1-carboxylate (1.00 g, 2.89 mmol) in dry DMF (8 mL), K$_2$CO$_3$ (0.798 g, 5.78 mmol) was added followed by a solution of 1-(bromomethyl)-4-phenoxy-benzene (0.911 g, 3.46 mmol) in DMF (1 mL) and the resulting mixture was stirred at room temperature for 46 h. The mixture was partitioned between EtOAc (70 mL) and water (60 mL). The organic phase was washed with brine (3×70 mL), dried over sodium sulfate, filtered and concentrated. The residue was purified by flash chromatography on Biotage KP-Sil SNAP cartridge (100% EtOAc) to afford title compound as a beige foam (1.380 g, 2.61 mmol, 90% yield). MS/ESI$^+$529.1 [MH]$^+$, Rt=25.4 min Step 4: synthesis of 1-[(4-phenoxyphenyl)methyl]-3-(3-piperidyl)pyrido[3,2-d]pyrimidine-2,4-dione

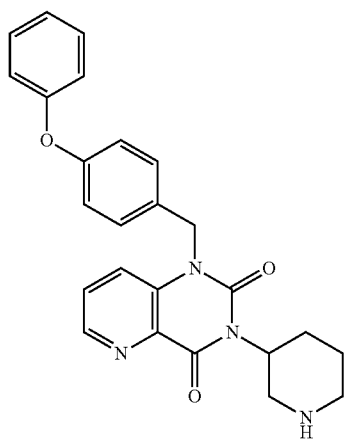 [SMILES: O=c1c2ncccc2n(Cc2ccc(Oc3ccccc3)cc2)c(=O)n1C1CCCNC1]

To a solution of tert-butyl 3-[2,4-dioxo-1-[(4-phenoxyphenyl)methyl]pyrido[3,2-d]pyrimidin-3-yl]piperidine-1-carboxylate (1.375 g, 2.60 mmol) in DCM (20 mL) cooled to 3° C., TFA (1.992 mL, 26.0 mmol) was added drop-wise and the resulting mixture was left to warm to r.t. and stirred for 6 h. The mixture was diluted with DCM and washed with sat. NaHCO$_3$. The organic phase was dried over sodium sulfate, filtered and concentrated to afford title compound as a beige foam (1.086 g, 2.53 mmol, 97% yield) which was used without purification. MS/ESI$^+$ 429.0 [MH]$^+$, Rt=8.9 min Step 5: synthesis of 1-[(4-phenoxyphenyl)methyl]-3-(1-prop-2-enoyl-3-piperidyl)pyrido[3,2-d]pyrimidine-2,4-dione

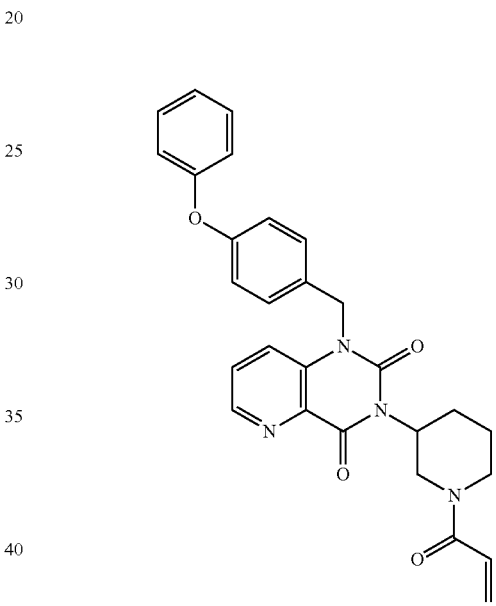

A solution of 1-[(4-phenoxyphenyl)methyl]-3-(3-piperidyl)pyrido[3,2-d]pyrimidine-2,4-dione (1.08 g, 2.52 mmol) and TEA (1.054 mL, 7.56 mmol) in DCM (20 mL) was cooled to 3° C. and acryloyl chloride (0.246 mL, 3.02 mmol) was added. The mixture was left to warm to r.t. and stirred overnight. The mixture was diluted with DCM and washed with 5% aqueous citric acid. The aqueous phase was extracted with DCM and the combined organic layers were washed with brine, dried over sodium sulfate, filtered and concentrated. The residue was purified by flash chromatography on Biotage KP-Sil SNAP cartridge (DCM to DCM:MeOH=95:5). A further purification by flash chromatography on Biotage Ultra silica SNAP cartridge (EtOAc to EtOAc:MeOH=95:5) was required to afford title compound as white foam (0.640 g, 1.326 mmol, 53% yield). MS/ESI$^+$ 483.1 [MH]$^+$, Rt=17.4 min; $^1$H NMR (300 MHz, DMSO-d$_6$) δ ppm 8.54, (d, 1H), 7.60-7.85 (m, 2H), 7.27-7.50 (m, 4H), 7.13 (t, 1H), 6.65-7.05 (m, 5H), 6.14 (d, 1H), 5.69 (d, 1H), 5.20-5.48 (m, 2H), 4.71-4.88 (m, 1H), 4.40-4.65 (m, 1H), 4.05-4.260 (m, 1H), 3.50-4.05 (m, 1H), 2.35-3.15 (m, 2H), 1.77-1.95 (m, 2H), 1.34-1.62 (m, 1H).

Example 2: Biological Characterization of Compound (I) EG-011

Cell Lines

Thirty-nine cell lines derived from activated B cell-like (ABC) (n=3) and germinal center B Cell (GCB) (n=12) diffuse large B cell lymphoma (DLBCL), mantle cell lymphoma (MCL) (n=9), chronic lymphocytic leukemia (CLL) (n=2), Hodgkin lymphoma (HL) (n=4), cutaneous T cell lymphoma (CTCL) (n=3), peripheral T cell lymphoma (PTCL) (n=1), anaplastic large T cell lymphoma (ALCL) (n=4), acute T cell leukemia (ATCL) (n=1) were cultured according to the recommended conditions. All media were supplemented with fetal bovine serum (10%), Penicillin-Streptomycin-Neomycin (~5,000 units penicillin, 5 mg streptomycin and 10 mg neomycin/mL, Sigma) and L-glutamine (1%).

Compounds

EG-011 was dissolved in dimethyl sulphoxide (DMSO) to obtain a stock concentration of 10 mM for in vitro experiments. EG-011 was dissolved in 25% hydroxypropyl beta cyclodextrin (HP-β-CD) in water and adjusted at pH 6.0 using NaOH (0.1 N) and HCl (0.1 N) for in vivo experiments. Application volume was 4.5 mL/kg (100 mg in 4.5 mL), and mice received 200 microliters (corresponding to 200 mg/kg) though intra peritoneal i.p. injection, once per day and five days per week.

Proliferation MTT Assay.

Cells were seeded in 96-well plates (non-tissue culture treated) at a density of 10,000 cells for all cell lines. Each compound was dissolved in dimethyl sulphoxide (DMSO). For treatment of cells, compounds were serially diluted in the appropriate tissue culture medium, at a range of 20 mcM-78 nM following a 1:2 dilution factor and added to cells (in three replicates). Cells were incubated for 72 hours at 37° C., 5% $CO_2$. DMSO alone was added to negative control (untreated) cells. Wells containing medium only were included on each plate and served as blanks for absorbance readings. MTT (Sigma-Aldrich Chemie GmbH, Buchs, Switzerland) was prepared as a 5 mg/ml stock in PBS and filter-sterilized. MTT solution (22 μL) was added to each well and tissue culture plates were incubated at 37° C. for 4 hours. Cells were then lysed with 25% SDS lysis buffer and absorbance was read at 570 nm using an AD340 plate reader (Beckman Coulter International SA, Switzerland). Absorbance values were expressed in percentage of proliferating cells in comparison with control cells (control corresponds to 100%).

Propidium Iodide Cell Cycle Staining Protocol

Lymphoma cells ($10^6$ per condition) were fixed in cold 70% ethanol (for at least 30 minutes at 4° C.), added dropwise to the cell pellet while vortexing. Cells were washed ×2 in PBS and Spin at 2000 rpm; supernatant was discarded and cells suspended in PBS (0.5 mL) and treated with Ribonuclease (50 μl of 100 μg/mL RNase). Then 200 μl of propidium iodide (50 μg/ml) were added and data acquisition was performed by using BD FACS-Canto II.

FITC Annexin V Apoptosis Assay

Lymphoma cells ($10^6$ per condition) were exposed to single agents for 72 h and assayed by FITC Annexin V Apoptosis Detection Kit (BD Biosciences) and by following the official protocol.

Xenograft Experiment

NOD-Scid (NOD.CB17-Prkdcscid/NCrHsd) mice were purchased from Harlan Laboratory (five-six weeks of age, approximately 20 g body weight). Mice maintenance and animal experiments were performed under institutional guidelines established for the Animal Facility and with study protocols approved by the local Cantonal Veterinary Authority. Mice were subcutaneously engrafted with $15\times10^6$ of human Mantle cell lymphoma REC1 cells and divided into two experimental groups. Starting with tumors of 180 mm$^3$ volume, mice underwent treatment with single agent while controls received vehicle only. EG-011 was administered 5 days per week at the dose of 200 mg/kg (200 microliters) though i.p. injection.

Data Mining

Binomial exact 95% confidence intervals (95% C.I.s) were calculated for median percentages. Differences in IC50 values among lymphoma subtypes were calculated using the t-Student test. Statistical significance was defined by P values of 0.05 or less.

Results

Figure 2:
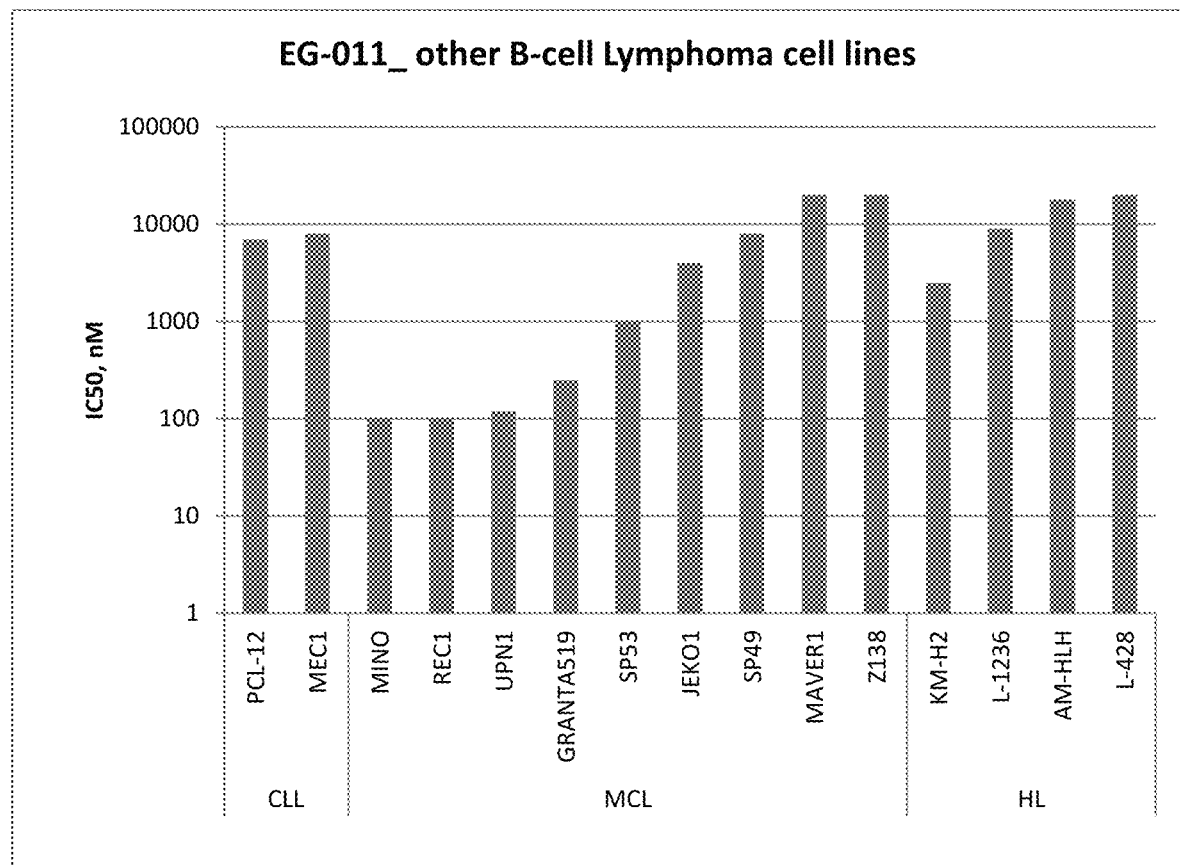
FIG. 2. Distribution of IC50 values for EG-011 in 2 PLL, 9 MCL and 4 HL cell lines. Cell lines were treated for 72 h. X-axis, PLL, chronic lymphocytic Leukemia; MCL, mantle cell lymphoma; HL, Hodgkin lymphoma. Y-axis, IC50 values in nM.
Figure 3:
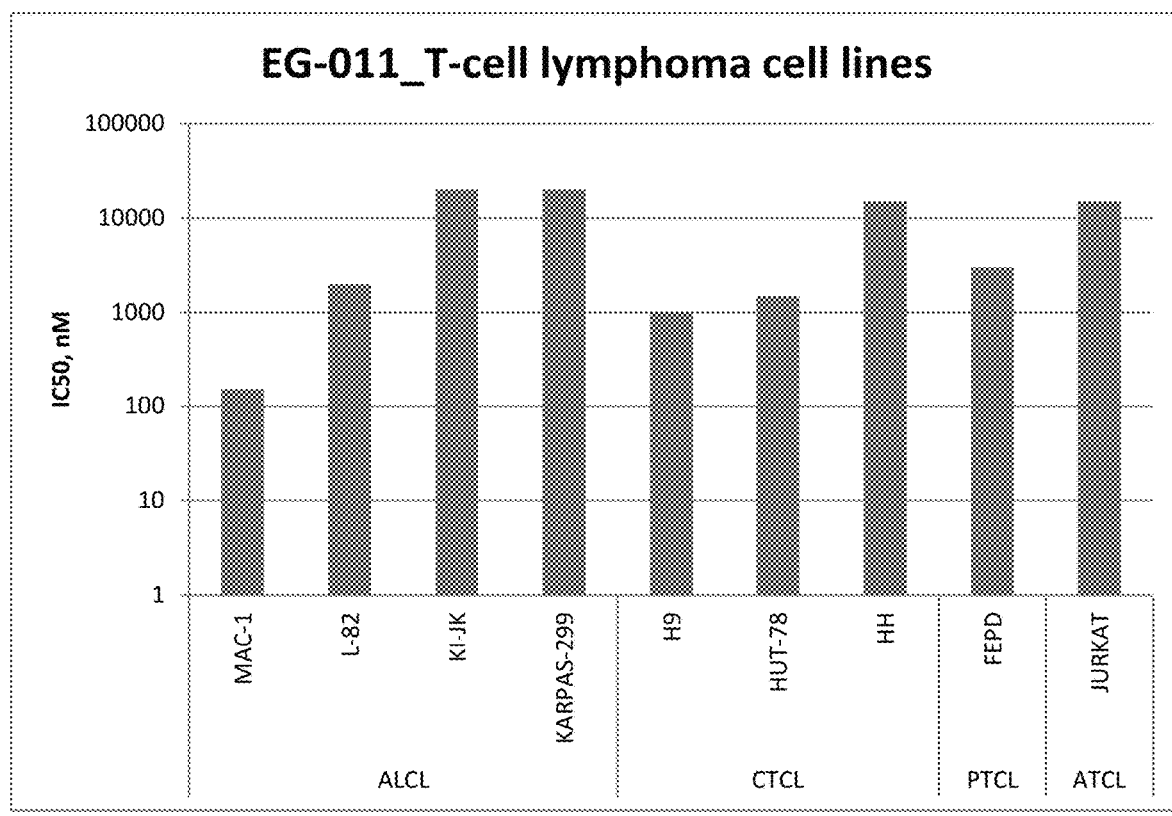
FIG. 3. Distribution of IC50 values for EG-011 in 2 PLL, 9 MCL and 4 HL cell lines. Cell lines were treated for 72 h. X-axis, ALCL, anaplastic large T cell lymphoma; CTCL, cutaneous T cell lymphoma; PTCL, peripheral T cell lymphoma; ATCL, acute T cell leukemia. Y-axis, IC50 values in nM.

EG-011 showed anti-tumor activity with a median IC50 of 2500 nM (95% C.I.; 100-20000 nM) across the 39 cell lines (Table 1). In particular, ABC-DLBCL presented a median IC50 of 10 μM, GCB-DLBCL 550 nM, MCL 1000 nM, HL 13.5 μM, PLL 7.5, T cell lymphomas (CTCL, PTCL, ALCL) 2.5 μM (FIGS. 1-3). As a whole, 12 out 39 cell lines showed IC50 values lower than 1 μM (95% C.I.; 100-600 nM). TP53, BCL2 and MYC were not associated with sensitivity/resistance across all the cell lines. Among GCB-DLBCL, representing the largest group, TP53 inactivation was detected in 5 out of 6 GCB-DLBCL sensitive (IC50s<600 nM) and in 3 out of 4 GCB-DLBCL resistant (IC50s>600 nM) cell lines (P=n.s.). BCL2 translocation was detected in 5 out of 6 GCB-DLBCL sensitive (IC50s<600 nM) and in 1 out of 3 GCB-DLBCL resistant (IC50s>600 nM) cell lines (P=n.s.). MYC translocation was detected in 3 out of 7 GCB-DLBCL sensitive (IC50s<600 nM) and in 1 out of 3 GCB-DLBCL resistant (IC50s>600 nM) cell lines (P=n.s.).

Figure 4:
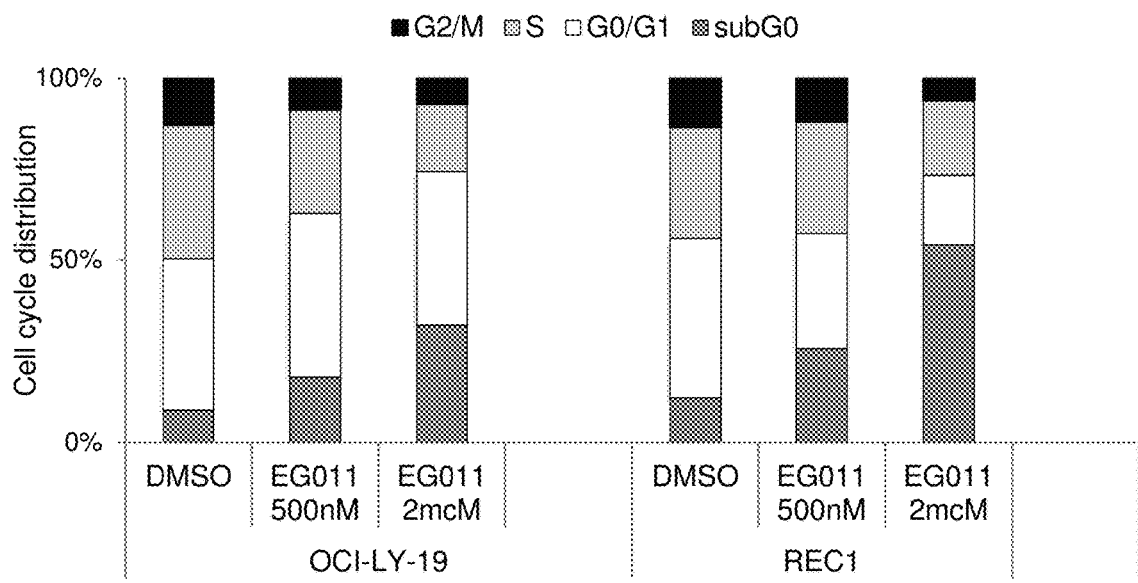
FIG. 4. Cell cycle phases distribution. OCI-LY-19 and REC1 were treated with two different concentration of EG-011 (500 and 2000 nM) for 72 h.
Figure 5:
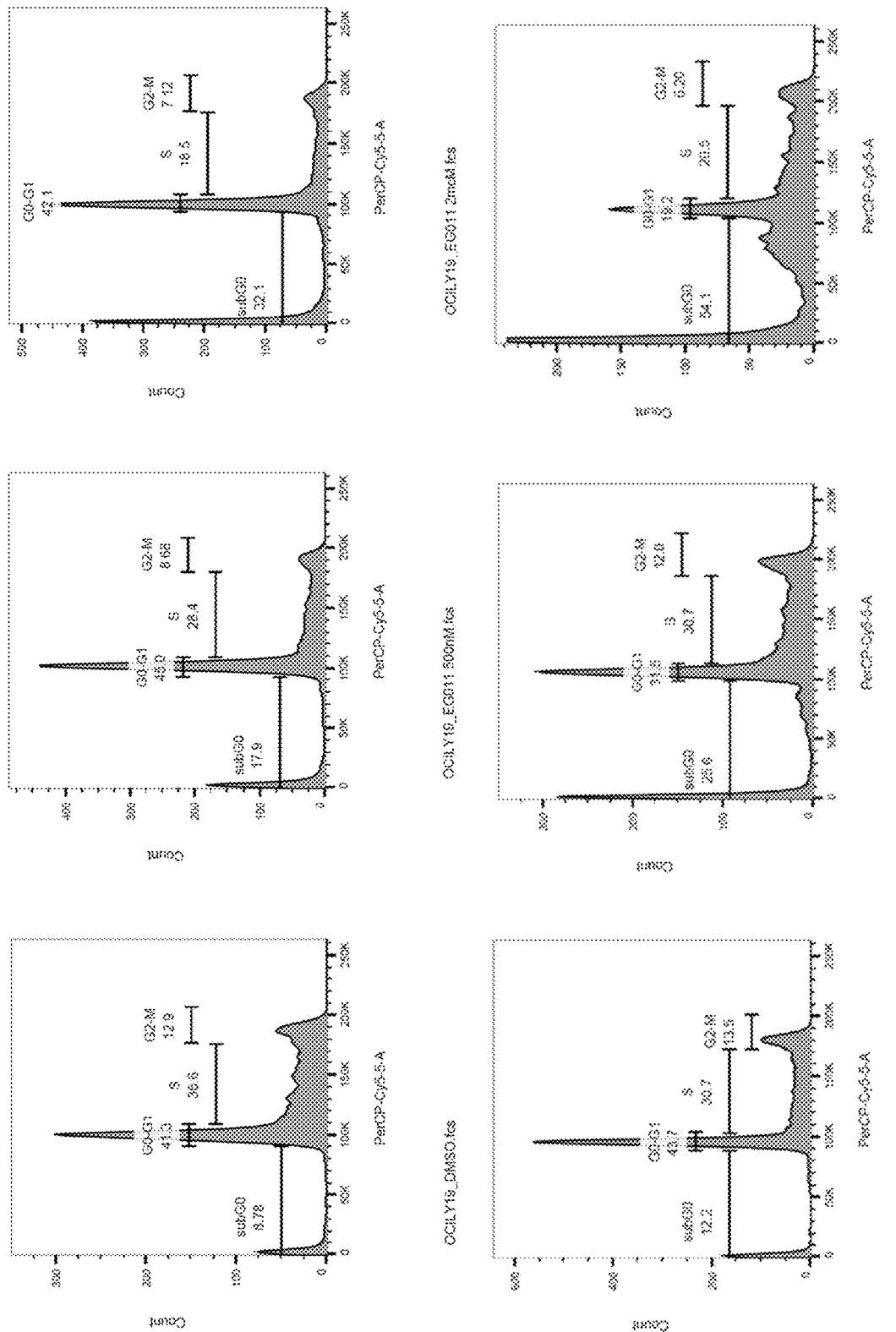
FIG. 5. Cell cycle peaks representation referred to the experiment reported in FIG. 4.

Two cell lines (OCI-LY-19 and REC1) were exposed to two concentrations of EG-011 (500 and 2000 nM) for 72 h, with a dose dependent increase of the cells in the sub-G0 phase (indicating dead cells) (FIGS. 4-5).

Figure 6:
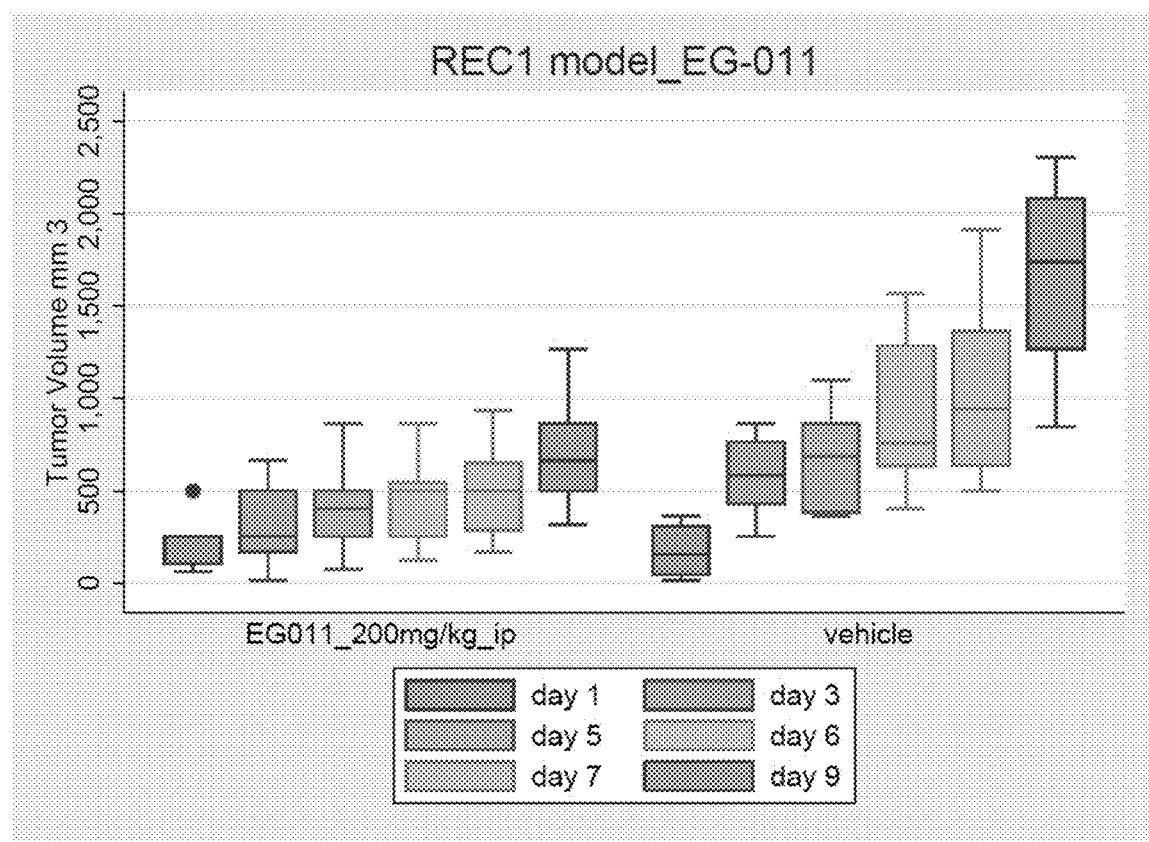
FIG. 6. Tumor volume distributions during the in vivo experiment with the REC1 model. Treatment with EG-011 started when tumors became visible (180 mm$^3$). Y-axis tumor volume expressed in mm$^3$. In each box-plot, the line in the middle of the box represents the median volume per day and the box extends from the 25th to the 75th percentile (interquartile range, IQ); the whiskers extend to the upper and lower adjacent values (i.e., ±1.5 IQ). Vehicle (N=8 mice), EG-011 (N=9 mice).
Figure 7:
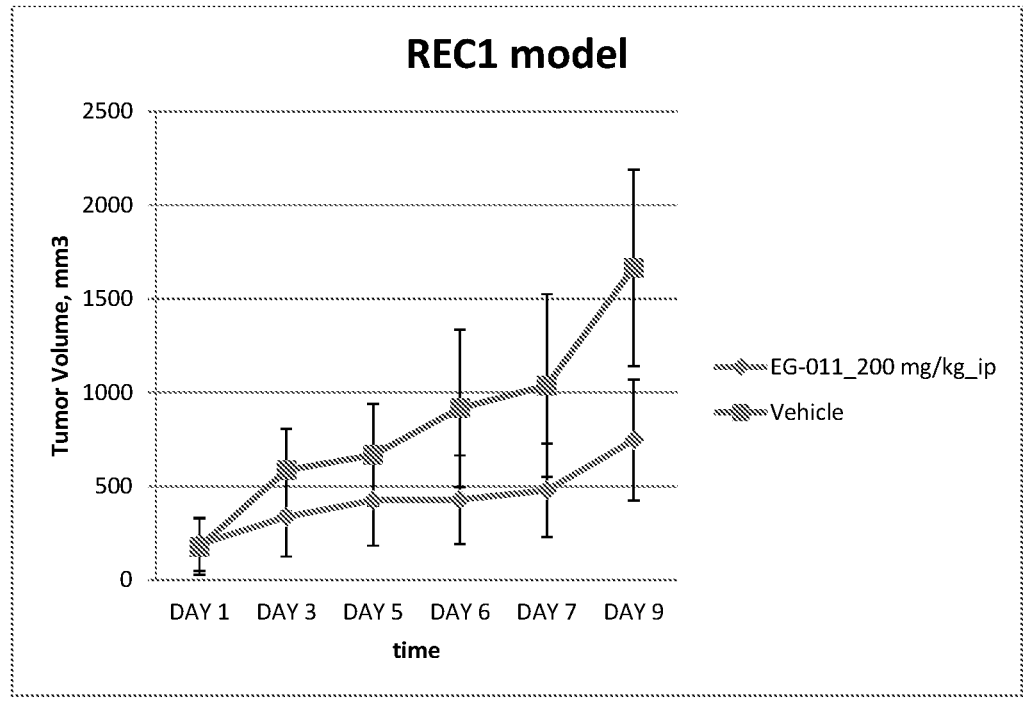
FIG. 7. Tumor volume averages during the experiment: REC1 model. Treatment with EG-011 started when tumors became visible (180 mm$^3$). Y-axis tumor volume expressed in mm$^3$.
Figure 8:
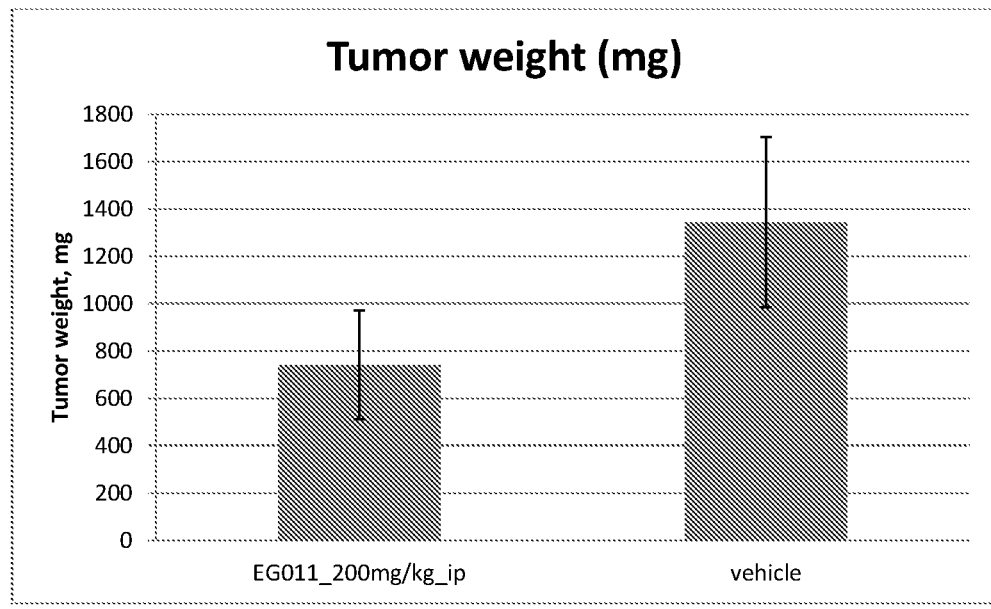
FIG. 8. The average tumor weight is reported together with standard deviation. P<0.001.

The anti-tumor activity of EG-011 as single agent was in vivo confirmed on a MCL model that has shown in vitro sensitivity, the REC1 cell line. EG-011 was administered at 200 mg/Kg once per day and 5 days per week. (FIG. 6 and FIG. 7). A group of mice of control was also used. EG-011 200 mg/Kg delayed tumor growth (volume) versus control (Day 6, Day 7, Day 9, P<0.05) and tumor weight (FIG. 8). There was no reduction in the body weight of animals treated with EG-011 confirming the lack of in vivo toxicity.

TABLE 1

IC50 values obtained from MTT assay with a 72 h exposure time on lymphoma cell lines.

| Cell line | | IC50 (nM) |
|---|---|---|
| MCL | MINO | 100 |
| MCL | REC1 | 100 |
| MCL | UPN1 | 120 |
| T Cell - ALCL | MAC-1 | 150 |
| GCB-DLBCL | OCI-LY-19 | 150 |
| GCB-DLBCL | OCI-LY-1 | 250 |
| MCL | GRANTA519 | 250 |
| GCB-DLBCL | OCI-LY-8 | 300 |
| GCB-DLBCL | SU-DHL-8 | 300 |
| GCB-DLBCL | SU-DHL-10 | 300 |
| GCB-DLBCL | SU-DHL-6 | 500 |
| GCB-DLBCL | TOLEDO | 600 |
| T Cell - CTCL | H9 | 1000 |
| MCL | SP53 | 1000 |
| T Cell - CTCL | HUT-78 | 1500 |

TABLE 1-continued

IC50 values obtained from MTT assay with a
72 h exposure time on lymphoma cell lines.

| Cell line | | IC50 (nM) |
|---|---|---|
| GCB-DLBCL | SU-DHL-16 | 1500 |
| GCB-DLBCL | Karpas-422 | 1500 |
| T Cell - ALCL | L-82 | 2000 |
| GCB-DLBCL | FARAGE | 2000 |
| HL | KM-H2 | 2500 |
| T Cell-PTCL | FEPD | 3000 |
| MCL | JEKO1 | 4000 |
| ABC-DLBCL | OCI-LY-10 | 5000 |
| GCB-DLBCL | OCI-LY-7 | 5000 |
| CLL | PCL-12 | 7000 |
| MCL | SP49 | 8000 |
| CLL | MEC1 | 8000 |
| HL | L-1236 | 9000 |
| ABC-DLBCL | OCI-LY-3 | 10000 |
| GCB-DLBCL | RCK8 | 10000 |
| T Cell Leukemia | JURKAT | 15000 |
| T Cell - CTCL | HH | 15000 |
| HL | AM-HLH | 18000 |
| ABC-DLBCL | SU-DHL-2 | 20000 |
| T Cell - ALCL | KI-JK | 20000 |
| T Cell - ALCL | KARPAS-299 | 20000 |
| HL | L-428 | 20000 |
| MCL | MAVER1 | 20000 |
| MCL | Z138 | 20000 |

The invention claimed is:

1. A compound of formula (I) or a pharmaceutically acceptable salt thereof,

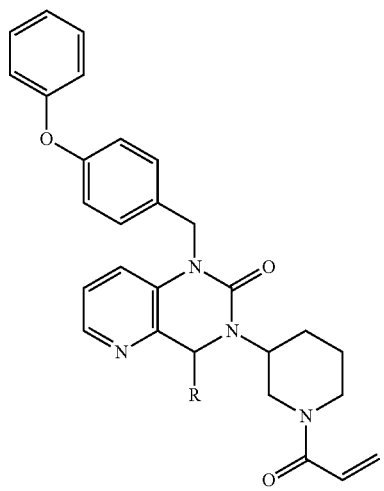

(I)

wherein —R represents =O or —H$_2$.

2. A pharmaceutical composition comprising the compound of formula (I) or pharmaceutically acceptable salt thereof as claimed in claim 1, in association with one or more pharmaceutically acceptable excipients.

3. The composition according to claim 2, wherein the compound of formula (I) or pharmaceutically acceptable salt thereof is present or administered at a dose between 10 and 500 mg/Kg.

4. The composition according to claim 2, wherein the compound of formula (I) or pharmaceutically acceptable salt thereof is present or administered at a dose between 100 and 300 mg/Kg.

5. The composition according to claim 2, wherein the compound of formula (I) or pharmaceutically acceptable salt thereof is formulated or co-administered with a further antitumor agent.

6. The composition according to claim 2, wherein the compound of formula (I) or pharmaceutically acceptable salt thereof is formulated for an administration route selected from: oral, peroral, buccal, sublingual, inhalatory, intramuscular, intravenous, topical, percutaneous, transcutaneous, and rectal.

7. A process for preparing a pharmaceutical composition according to claim 2, comprising contacting the compound of formula (I) or salt thereof, with the one or more pharmaceutically acceptable excipients.

8. A process to obtain a compound of formula (I) as defined in claim 1, comprising reacting a compound of formula (II), wherein —R is —H$_2$ or =O

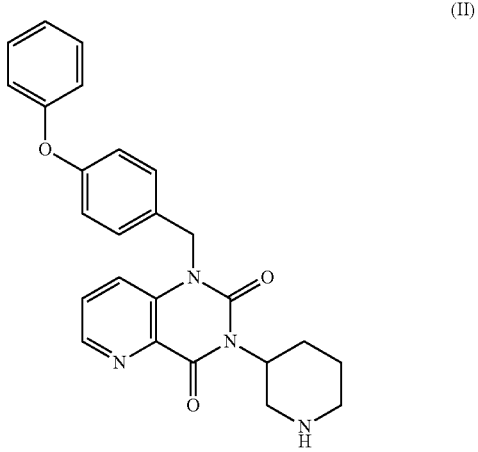

(II)

with acryloyl chloride.

9. A method of treatment comprising administering a compound of formula (I) or a pharmaceutically acceptable salt thereof,

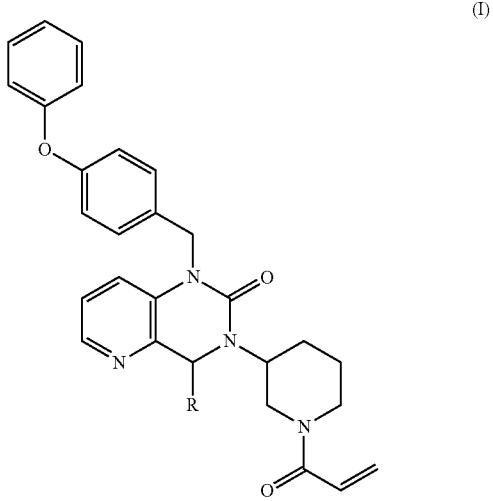

(I)

where —R represents =O or —H$_2$, wherein the treatment is for a disease selected from the group consisting of carcinomas, lymphomas, leukernias, sarcomas, myelomas, and corresponding mixed-type forms.

10. The method according to claim 9, wherein the treatment is for a disease selected from the group consisting of chronic lymphocytic leukemia, T cell leukemia, T cell lymphomas, B cell leukemia, B cell lymphomas, mantle cell lymphoma, Hodgkin lymphoma, and non-Hodgkin lymphoma.

11. The method according to claim 10, wherein the T cell leukemia is an acute T cell leukemia.

12. The method according to claim 10, wherein the T cell lymphomas include cutaneous T-cell lymphomas, peripheral T cell lymphomas, and anaplastic large T cell lymphomas.

13. The method according to claim 10, wherein the B cell lymphomas include diffuse large B cell lymphomas and diffuse large B cell lymphomas.

14. The method according to claim 13, wherein the diffuse large B cell lymphomas includes activated B cell-like diffuse large B cell lymphomas, and germinal center B cell diffuse large B cell lymphomas.

\* \* \* \* \*